US012773326B2

(12) United States Patent
Schifano et al.

(10) Patent No.: US 12,773,326 B2
(45) Date of Patent: Oct. 27, 2026

(54) SURGICAL TOOLS AND METHODS FOR ACCESSING A SACROILIAC JOINT VIA A POSTERIOR APPROACH BASED ON SENSED ELECTRICAL CHARACTERISTICS

(71) Applicants: SpineGuard, Vincennes (FR); Omnia Medical, LLC, Morgantown, WV (US)

(72) Inventors: Troy Schifano, Morgantown, WV (US); Stephane Bette, Vincennes (FR)

(73) Assignees: SpineGuard, Vincennes (FR); Omnia Medical, LLC, Morgantown, WV (US)

(*) Notice: Subject to any disclaimer, the term of this patent is extended or adjusted under 35 U.S.C. 154(b) by 0 days.

(21) Appl. No.: 19/242,779

(22) Filed: Jun. 18, 2025

(65) Prior Publication Data

US 2026/0007528 A1 Jan. 8, 2026

Related U.S. Application Data

(60) Provisional application No. 63/668,085, filed on Jul. 5, 2024.

(51) Int. Cl.

| | |
|---|---|
| ***A61F 2/46*** | (2006.01) |
| ***A61B 17/17*** | (2006.01) |
| *A61B 17/00* | (2006.01) |

(52) U.S. Cl.

CPC ........ *A61F 2/4611* (2013.01); *A61B 17/1796* (2013.01); *A61F 2/4657* (2013.01);

(Continued)

(58) Field of Classification Search

CPC ........ A61B 17/1796; A61B 2017/0003; A61B 2017/00079; A61B 2017/00128;

(Continued)

(56) References Cited

U.S. PATENT DOCUMENTS

| | | | |
|---|---|---|---|
| 5,334,205 | A | 8/1994 | Cain |
| 6,337,994 | B1 | 1/2002 | Stoianovici et al. |

(Continued)

FOREIGN PATENT DOCUMENTS

| | | | |
|---|---|---|---|
| CN | 1929789 | A | 3/2007 |
| CN | 103948412 | A | 7/2014 |

(Continued)

OTHER PUBLICATIONS

Balmer, et al., Characterization of the Electrical Conductivity of Bone And Its Correlation To Osseous Structure, Scientific Reports, 8:8601 (2018).

(Continued)

*Primary Examiner* — Sameh R Boles

(74) *Attorney, Agent, or Firm* — Greenberg Traurig, LLP; Christopher C. Bolten; Albert K. Heng

(57) ABSTRACT

The present disclosure provides systems including a cannulated surgical drill tool with electrical conductivity sensing capabilities, and surgical techniques for using such tools in minimally invasive surgical procedures for accessing the SI joint via a posterior approach using an electrical conductivity feedback to facilitate accurate placement into or across the SI joint. For example, the cannulated surgical drill tool may include one or more pairs of electrodes at its distal penetration tip configured to measure electrical conductivity of tissue in contact with the distal tip during a drilling procedure and may emit an alert indicative of the measured electrical conductivity, and accordingly, the type of tissue in contact with the distal tip of the cannulated surgical drill tool, in real-time.

22 Claims, 10 Drawing Sheets

(52) U.S. Cl.
CPC ................. *A61B 2017/0003* (2013.01); *A61B 2017/00079* (2013.01); *A61B 2017/00128* (2013.01); *A61F 2002/4662* (2013.01); *A61F 2002/4677* (2013.01); *A61F 2002/4681* (2013.01); *A61F 2002/469* (2013.01)

(58) Field of Classification Search
CPC .................. A61F 2/4657; A61F 2/4611; A61F 2002/4662; A61F 2002/4677; A61F 2002/4681; A61F 2002/469
See application file for complete search history.

(56) References Cited

U.S. PATENT DOCUMENTS

| | | | |
|---|---|---|---|
| 6,470,207 | B1 | 10/2002 | Simon et al. |
| 6,635,062 | B2 | 10/2003 | Ray, III et al. |
| 6,796,985 | B2 | 9/2004 | Bolger et al. |
| 7,580,743 | B2 | 8/2009 | Bourlion et al. |
| 8,092,457 | B2 | 1/2012 | Oettinger et al. |
| 8,221,428 | B2 | 7/2012 | Trieu |
| 8,361,152 | B2 | 1/2013 | McCormack et al. |
| 8,419,746 | B2 | 4/2013 | Bourlion et al. |
| 8,486,119 | B2 | 7/2013 | Bourlion |
| 8,634,897 | B2 | 1/2014 | Simon et al. |
| 8,795,285 | B2 | 8/2014 | Kwon |
| 8,939,979 | B2 | 1/2015 | Del Rio et al. |
| 9,066,751 | B2 | 6/2015 | Sasso |
| 9,119,732 | B2 | 9/2015 | Schifano et al. |
| 9,204,830 | B2 | 12/2015 | Zand et al. |
| 9,538,935 | B2 | 1/2017 | Bourlion et al. |
| 9,855,060 | B2 | 1/2018 | Ardel et al. |
| 9,901,283 | B2 | 2/2018 | Bourlion et al. |
| 9,937,009 | B2 | 4/2018 | Schroeder et al. |
| 10,064,630 | B2 | 9/2018 | Forman et al. |
| 10,092,300 | B2 | 10/2018 | Del Rio et al. |
| 10,149,729 | B2 | 12/2018 | Smaby et al. |
| 10,624,572 | B2 | 4/2020 | Bourlion et al. |
| 10,987,113 | B2 | 4/2021 | Mcginley et al. |
| 11,000,292 | B2 | 5/2021 | Mcginley |
| 11,058,436 | B2 | 7/2021 | Mcginley et al. |
| 11,083,469 | B2 | 8/2021 | Del Rio et al. |
| 11,344,372 | B2 | 5/2022 | Bourlion et al. |
| 11,399,902 | B2 | 8/2022 | Bourlion et al. |
| 12,161,348 | B2 | 12/2024 | Lorian et al. |
| 12,213,683 | B2 | 2/2025 | Del Rio et al. |
| 2002/0120197 | A1 | 8/2002 | Kleffner et al. |
| 2003/0078495 | A1 | 4/2003 | Goodwin |
| 2005/0116673 | A1 | 6/2005 | Carl et al. |
| 2005/0119660 | A1 | 6/2005 | Bourlion et al. |
| 2006/0241628 | A1 | 10/2006 | Parak |
| 2007/0218420 | A1 | 9/2007 | Syribeys |
| 2007/0239187 | A1 | 10/2007 | Brunnett et al. |
| 2008/0086140 | A1 | 4/2008 | Wolf |
| 2008/0262526 | A1 | 10/2008 | Neubardt et al. |
| 2009/0157059 | A1 | 6/2009 | Allen et al. |
| 2010/0024981 | A1 | 2/2010 | Wallace et al. |
| 2010/0286694 | A1 | 11/2010 | Rio et al. |
| 2011/0015649 | A1 | 1/2011 | Anvari et al. |
| 2012/0046668 | A1 | 2/2012 | Gantes |
| 2012/0296213 | A1 | 11/2012 | Mauldin, Jr. et al. |
| 2012/0296428 | A1* | 11/2012 | Donner .............. A61B 17/7043 623/17.11 |
| 2013/0085413 | A1 | 4/2013 | Tsamir et al. |
| 2013/0085505 | A1 | 4/2013 | Markey et al. |
| 2013/0152746 | A1 | 6/2013 | Kerboul et al. |
| 2013/0296734 | A1 | 11/2013 | Bourlion et al. |
| 2014/0094808 | A1 | 4/2014 | Herndon |
| 2014/0276002 | A1 | 9/2014 | West et al. |
| 2014/0276839 | A1 | 9/2014 | Forman et al. |
| 2014/0276950 | A1 | 9/2014 | Smaby et al. |
| 2014/0324044 | A1 | 10/2014 | Haufe et al. |
| 2015/0066030 | A1 | 3/2015 | Mcginley et al. |
| 2015/0148176 | A1 | 5/2015 | Schroeder et al. |
| 2015/0196306 | A1 | 7/2015 | Del Rio et al. |
| 2015/0366624 | A1 | 12/2015 | Kostrzewski et al. |
| 2016/0074123 | A1 | 3/2016 | Bly et al. |
| 2016/0302871 | A1 | 10/2016 | Gregerson et al. |
| 2016/0361069 | A1 | 12/2016 | Ardel et al. |
| 2017/0007199 | A1 | 1/2017 | Bourlion et al. |
| 2017/0056116 | A1 | 3/2017 | Kostrzewski |
| 2017/0100822 | A1 | 4/2017 | Cutler |
| 2017/0360493 | A1 | 12/2017 | Zucker et al. |
| 2018/0042514 | A1 | 2/2018 | Verard et al. |
| 2018/0098714 | A1 | 4/2018 | Bourlion et al. |
| 2018/0177556 | A1 | 6/2018 | Noonan |
| 2018/0242985 | A1 | 8/2018 | Vipperman et al. |
| 2019/0175886 | A1 | 6/2019 | Abdelwahed et al. |
| 2019/0201011 | A1 | 7/2019 | Del Rio et al. |
| 2019/0388173 | A1 | 12/2019 | Pak et al. |
| 2020/0324408 | A1 | 10/2020 | Bourlion et al. |
| 2020/0337782 | A1 | 10/2020 | Glassman et al. |
| 2021/0068905 | A1 | 3/2021 | Quaid et al. |
| 2021/0282862 | A1 | 9/2021 | Bourlion et al. |
| 2022/0022891 | A1 | 1/2022 | Del Rio et al. |
| 2022/0104901 | A1 | 4/2022 | Lawrie |
| 2022/0168048 | A1 | 6/2022 | Shoham et al. |
| 2022/0175455 | A1 | 6/2022 | Ungi et al. |
| 2022/0175462 | A1 | 6/2022 | Turgeman et al. |
| 2022/0218421 | A1 | 7/2022 | Junio et al. |
| 2022/0361896 | A1 | 11/2022 | Bette et al. |
| 2022/0409214 | A1 | 12/2022 | Lorian et al. |
| 2023/0134461 | A1 | 5/2023 | Casey et al. |
| 2024/0237994 | A1 | 7/2024 | Chandanson et al. |

FOREIGN PATENT DOCUMENTS

| | | | |
|---|---|---|---|
| CN | 110882037 | A | 3/2020 |
| EP | 1474046 | A1 | 11/2004 |
| EP | 3319539 | A1 | 5/2018 |
| EP | 3525696 | A1 | 8/2019 |
| EP | 3761870 | A1 | 1/2021 |
| EP | 3883491 | A1 | 9/2021 |
| FR | 2795624 | A1 | 1/2001 |
| FR | 3034643 | A1 | 10/2016 |
| JP | 2005525150 | A | 8/2005 |
| JP | 2016518878 | A | 6/2016 |
| WO | WO-03068076 | A1 | 8/2003 |
| WO | WO-2014146090 | A1 | 9/2014 |
| WO | WO-2015006296 | A1 | 1/2015 |
| WO | WO-2016043676 | A1 | 3/2016 |
| WO | WO-2016162634 | A1 | 10/2016 |
| WO | WO-2016199152 | A1 | 12/2016 |
| WO | WO-2019002578 | A1 | 1/2019 |
| WO | WO-2020000038 | A1 | 1/2020 |
| WO | WO-2020097481 | A1 | 5/2020 |
| WO | WO-2021046247 | A1 | 3/2021 |
| WO | WO-2021111439 | A1 | 6/2021 |
| WO | WO-2022170185 | A1 | 8/2022 |

OTHER PUBLICATIONS

International Search Report & Written Opinion dated Aug. 31, 2022 in Int'l PCT Patent Appl. Serial No. PCT/EP2022/061868.
International Search Report & Written Opinion dated Oct. 1, 2024 in Int'l PCT Patent Appl. Serial No. PCT/EP2024/017206.
International Search Report & Written Opinion dated Dec. 15, 2022 in Int'l PCT Patent Appl. No. PCT/IB2022/059201.
International Search Report and Written Opinion for PCT Application No. PCT/IL2020/051241, mailed Mar. 22, 2021, 13 pages.
International Search Report and Written Opinion for PCT Application No. PCT/IL2022/050585, mailed Nov. 3, 2022, 15 pages.
International Search Report for PCT Application No. PCT/FR2015/050241 mailed May 4, 2015, 08 Pages.
Int'l Search Report & Written Opinion dated Jan. 7, 2019 in Int'l PCT Patent Appl. Serial No. PCT/FR2018/052640.

* cited by examiner

SURGICAL TOOLS AND METHODS FOR ACCESSING A SACROILIAC JOINT VIA A POSTERIOR APPROACH BASED ON SENSED ELECTRICAL CHARACTERISTICS

CROSS-REFERENCE TO RELATED APPLICATION

This application claims priority to U.S. Prov. Patent Appl. No. 63/668,085, filed Jul. 5, 2024, the entire contents of which are incorporated herein by reference.

FIELD OF THE INVENTION

The present technology relates generally to musculoskeletal surgical tools for accessing the sacroiliac joint and methods of use thereof.

BACKGROUND

The Sacroiliac (SI) joint is located at the juncture of the ilium (or iliac wing) and the sacrum at the base of the pelvis, and is supported by a range of ligaments including, for example, the sacroiliac ligament at the base of the joint and the anterior sacroiliac ligament at the top of the joint. While the SI joint has a limited range of motion, dysfunction of the SI joint has been identified as a cause for chronic lower back pain. Contributing factors include post traumatic injury, accelerated wear/instability after lumbar fusion, post pregnancy pain/instability, and longer life span combined with a more active lifestyle in many patients. As the SI joint is increasingly being diagnosed as a common pain generator, SI joint degenerative disease and instability are being diagnosed and treated more commonly. If non-surgical treatments fail to provide relief, SI joint fusion is a treatment option. The primary surgical objective of all SI joint fusion procedures is to provide immediate stabilization within the joint space to support osseous consolidation and the development of a mechanically solid arthrodesis. Posterior Sacroiliac Fusion (PSIF) consists of inserting an implant or an allograft into or across the intra-articular space of the SI joint.

From a lateral view, the SI joint is fully enclosed between the iliac wing and the sacrum, and occluded for direct visualization by the iliac wing. From an inferior view, the SI joint is occluded from direct visualization due to the anatomy of the sacrum, the ilium, and the pelvis. The SI joint can be fully observed between the iliac wing and the sacrum from a frontal (e.g., anterior) view, and from a top down (e.g., superior) view where the posterior superior iliac crest and the entry point of the S1 pedicle can also be observed in a direct line from one another. The SI joint is not fully exposed for direct visualization from a rear (e.g., posterior) view due to the angled and raised iliac crest of the iliac wing; however, this angle provides a landmark for the entry point of the surgical tools described herein at the posterior iliac crest. Thus, direct visualization of the SI joint can only be achieved through an anterior, superior, or posterior-oblique view of the sacrum and pelvis.

However, due to major organs being present in the pelvic-sacral cavity (colon, rectum, bladder, etc.), an anterior or superior approach to the bony anatomy and, specifically the SI joint, are unreasonable in risk. Accordingly, PSIF procedures are commonly performed via two approaches: lateral transfixing or posterior intra-articular. For example, lateral approaches can be performed as described in U.S. Pat. Nos. 5,334,205 and 8,221,428, the entire contents of each of which are incorporated by reference. However, these techniques rely on non-direct confirmation methods such as navigation and fluoroscopy to determine accurate landmark and SI joint locations. While the posterior approach is more straightforward with less risk, precise implant placement is paramount.

Precise insertion of an implant into or across the SI joint is largely difficult due to the complex geometry of the SI joint. In addition, current techniques and instrumentation systems may require extensive surgical exposure and dissection. Incorrect placement of an implant into or across the targeted SI joint may cause the implant to protrude excessively on either the sacrum or ilium, resulting in poor or no fusion and/or subsidence of the implants ilium. Accordingly, procedure failure is frequent due to incorrect implant placement into or across the SI joint, which may require additional revision surgery to correct misplacement of the implant.

In view of the foregoing drawbacks of previously known systems and methods, there exists a need for surgical tools and methods for precisely accessing the SI joint via a posterior approach for treatment thereof.

SUMMARY

The present disclosure overcomes the drawbacks of previously-known systems and methods by providing improved methods for accessing the Sacroiliac (SI) joint via a posterior approach, and associated surgical tools for facilitating the procedure. In accordance with one aspect of the present disclosure, a method for accessing a patient's Sacroiliac (SI) joint via a posterior approach is provided. The method may include: identifying an anatomical landmark associated with the patient's SI joint to locate the SI joint, the anatomical landmark disposed on a posterior side of the SI joint; identifying an incision site on the posterior side of the SI joint based on the anatomical landmark; advancing a distal tip of a cannulated instrument through the incision site towards a target position in an intra-articular space of the SI joint while monitoring an alert signal generated by the cannulated instrument, the alert signal indicative of electrical conductivity of tissue in contact with the distal tip in real-time; removing, if the alert signal indicates low electrical conductivity, the cannulated instrument from the patient's SI joint and reinserting the distal tip of the cannulated instrument through another identified incision site towards the target position while monitoring the alert signal generated by the cannulated instrument; advancing, if the alert signal indicates high electrical conductivity, the distal tip of the cannulated instrument towards the target location; adjusting, if the alert signal indicates low electrical conductivity, a position of the cannulated instrument relative to the SI joint to redirect the cannulated instrument towards the target location; and advancing, if the alert signal indicates high electrical conductivity, the distal tip of the cannulated instrument until the distal tip of the cannulated instrument is disposed at the target location.

Identifying the anatomical landmark associated with the patient's SI joint may comprise identifying a right posterior iliac crest of the patient. In addition, advancing the distal tip of the cannulated instrument through the incision site to the target position in the intra-articular space of the SI joint may comprise manually applying a force to a proximal end of the cannulated instrument. Alternatively, or additionally, advancing the distal tip of the cannulated instrument through the incision site to the target position in the intra-articular space of the SI joint may comprise applying a force to a proximal end of the cannulated instrument via a surgical hammer tool. Moreover, monitoring the alert signal generated by the cannulated instrument may comprise monitoring at least one of an audible or visual alert emitted based on the alert signal. For example, at least one of a pitch or cadence of the audible alert may be based on the electrical conductivity of tissue in contact with the distal tip in real-time. Additionally, or alternatively, at least one of a frequency, intensity, or color of the visual alert may be based on the electrical conductivity of tissue in contact with the distal tip in real-time.

The alert signal may be indicative of a type of tissue in contact with the distal tip of the cannulated instrument in real-time. For example, the alert signal may indicate that the distal tip of the cannulated instrument is in contact with at least one of an ilium or a sacrum when the alert signal indicates low electrical conductivity. In some embodiments, the alert signal indicates that the distal tip of the cannulated instrument is in contact with connective tissue adjacent to the SI joint when the alert signal indicates low electrical conductivity. Moreover, the cannulated instrument may be configured to transmit data indicative of the electrical conductivity to an external display device. The external display device may be configured to graphically display the data indicative of the electrical conductivity. Accordingly, monitoring the alert signal generated by the cannulated instrument may comprise monitoring at least one of an audible or visual alert emitted by the external display device based on the alert signal.

In some embodiments, adjusting the position of the cannulated instrument relative to the SI joint to redirect the cannulated instrument towards the target location may comprise: removing the cannulated instrument from the patient; reorienting the distal tip of the cannulated instrument relative to the SI joint; and reinserting the distal tip of the cannulated instrument through the incision site towards the target position in the intra-articular space of the SI joint. Additionally, or alternatively, adjusting the position of the cannulated instrument relative to the SI joint to redirect the cannulated instrument towards the target location may comprise reorienting the distal tip of the cannulated instrument relative to the SI joint, e.g., to adjust the trajectory of the cannulated instrument within the SI joint. The distal tip of the cannulated instrument comprises one or more pairs of electrodes configured to sense the electrical conductivity of tissue in contact with the distal tip. The method further may comprise visualizing advancement of the cannulated instrument through the SI joint via fluoroscopy. Additionally, the method may comprise monitoring a depth of advancement of the cannulated instrument through the SI joint via a plurality of markers disposed on an outer surface of the cannulated instrument.

The method further may comprise: inserting a distal end of a K-wire through a lumen of the cannulated instrument to the target position in the intra-articular space of the SI joint, such that a proximal end of the K-wire extends external to the patient; and removing the cannulated instrument from the patient. The cannulated instrument may comprise a cannula and a stylet removably disposed within a lumen of the cannula, the stylet comprising the distal tip of the cannulated instrument. Accordingly, the method further may comprise removing the stylet from the lumen of the cannula when the distal tip is disposed at the target position in the intra-articular space of the SI joint. Accordingly, inserting the distal end of the K-wire through the lumen of the cannulated instrument to the target position in the intra-articular space of the SI joint may comprise inserting the distal end of the K-wire through the lumen of the cannula. In addition, the method further may comprise advancing a surgical tool over the K-wire to the target position in the intra-articular space of the SI joint to perform a surgical procedure at the target position. Additionally, or alternatively, the method may comprise advancing a spinal implant over the K-wire to the target position into or across the intra-articular space of the SI joint.

DETAILED DESCRIPTION

The present disclosure provides systems including a cannulated surgical drill tool, and surgical techniques for using such tools in minimally invasive surgical procedures for accessing the SI joint via a posterior-oblique approach using an electrical conductivity feedback to facilitate accurate placement into the SI joint. By using a posterior-oblique approach, the surgeon may use the right posterior iliac crest as an anatomical landmark to identify the corresponding access site to the S1 pedicle, as described in U.S. Pat. No. 9,119,732, the entire contents of which are incorporated by reference herein. The cannulated surgical drill tools described herein may be used during SI joint pilot hole drilling to provide feedback to the surgeon via visual and audible alerts that indicate electrical conductivity values and/or a change in electrical conductivity at the tip of the cannulated surgical drill tool, as well as contact of the tip with bone and possible cortex perforation. Further, the cannulated surgical drill tool may be used with fluoroscopic guidance in percutaneous (MIS) surgical approaches of the SI joint.

Figure 1:
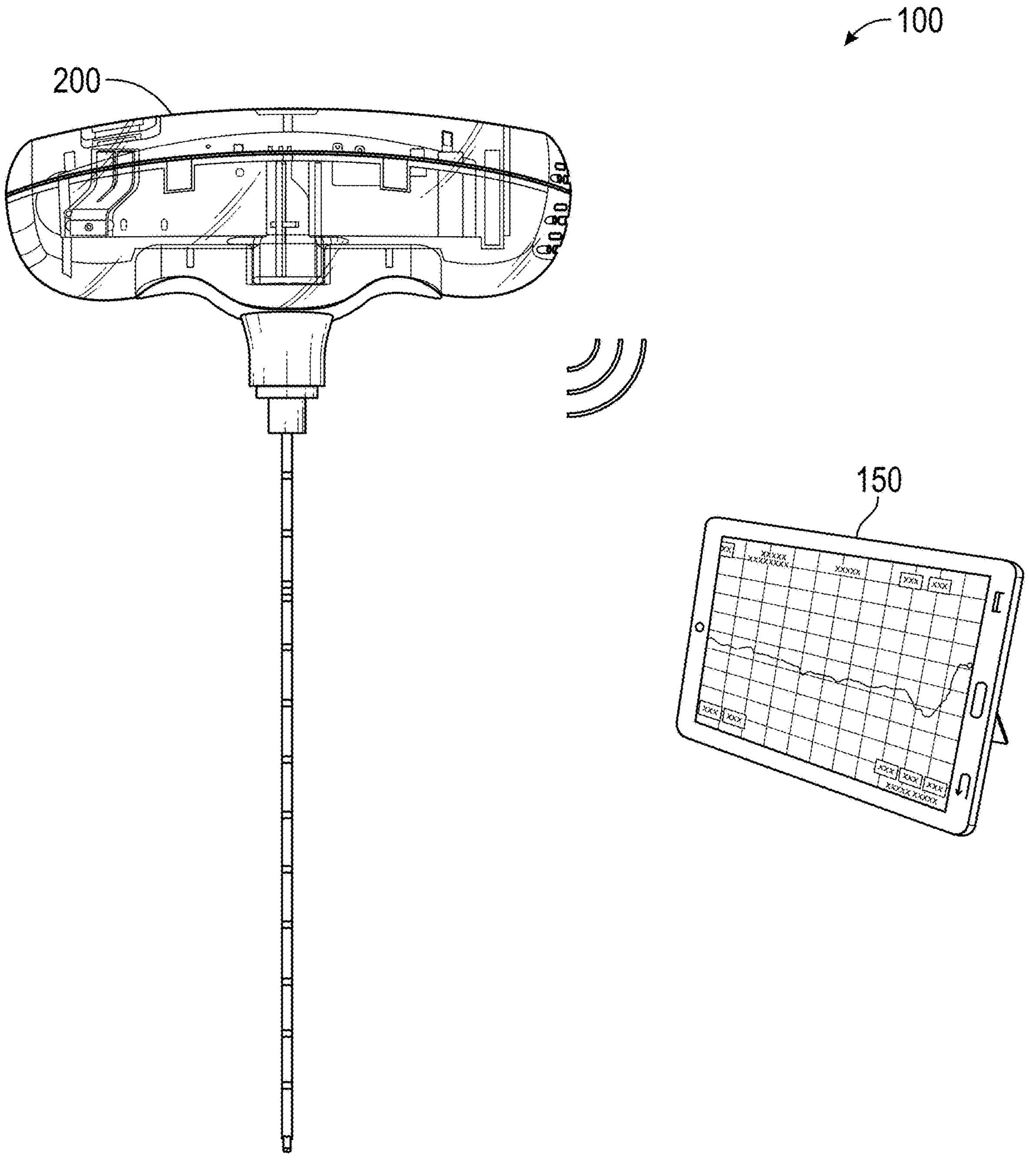
FIG. 1 illustrates an exemplary system for accessing the SI joint based on sensed electrical characteristics in accordance with the principles of the present disclosure.

Referring now to FIG. 1, an exemplary system for accessing the SI joint via a posterior-oblique approach based on sensed electrical characteristics is provided. As shown in FIG. 1, system 100 may include cannulated surgical instrument 200 configured for creating a hole, e.g., a pilot hole, in the SI joint while monitoring sensed electrical characteristics (e.g., electrical values associated with electrical conductivity, conductance, resistivity, resistance, impedance, etc.) during penetration to prevent undesirable/inadvertent drilling into nearby anatomical structures such as the ilium or sacrum (e.g., cortex perforation). For example, cannulated instrument 200 may be a drill, needle, pin, nail, burr, threaded tool, tap, probe, square awl, spatula, curette, chisels, blade, etc. Cannulated instrument 200 further may be configured for placement of a wire (e.g., a Kirschner wire ("K-wire")) at a target location in the SI joint to facilitate a further surgical procedure at the SI joint. For example, upon placement of the K-wire, cannulated instrument 200 may be removed over the K-wire such that the K-wire remains implanted and extends from the target location within the SI joint external to the patient. Accordingly, one or more additional surgical tools may be advanced over the K-wire to access the SI joint. The additional surgical tools may include, for example, a dilator, a box chisel and/or a rasp to expand and clear tissue from the void in the SI joint, a surgical drill for preparing the SI joint for an implant and/or graft material insertion, a bone graft, an implant (e.g., a polyether ether ketone (PEEK) implant, a titanium implant, an implant comprising a biological material other than bone, etc.), a joint repairing device, a device for delivering therapeutic materials (e.g., bone morphogenetic proteins (BMP), demineralized bone matrix (DBM), stem cells, etc.) to improve recovery and growth of the bone at the SI joint, etc.

Cannulated instrument 200 is configured to sense electrical conductivity at its distal tip during penetration, e.g., via one or more pairs of electrodes as described in further detail below, and emit an audible and/or visual alert indicating the sensed electrical conductivity values and/or a change in sensed electrical conductivity. Accordingly, cannulated instrument 200 may include electrical components necessary to receive and measure electrical signals from the electrodes (e.g., a conductivity meter), as well as to emit the audible and/or visual alerts (e.g., an alert device such as an audio speaker and/or LED light). In some embodiments, system 100 further may include display device 150 configured to wirelessly communicate with cannulated instrument 200 to receive data indicative of the sensed electrical conductivity, and to display and/or record the received data. For example, as shown in FIG. 1, display device 150 may include a display (e.g., a graphical user interface) for graphically displaying the sensed electrical conductivity in real-time. Accordingly, cannulated instrument 200 further may include a wireless communication module for communicating data to display device 150, as described in further detail below.

Figure 2:
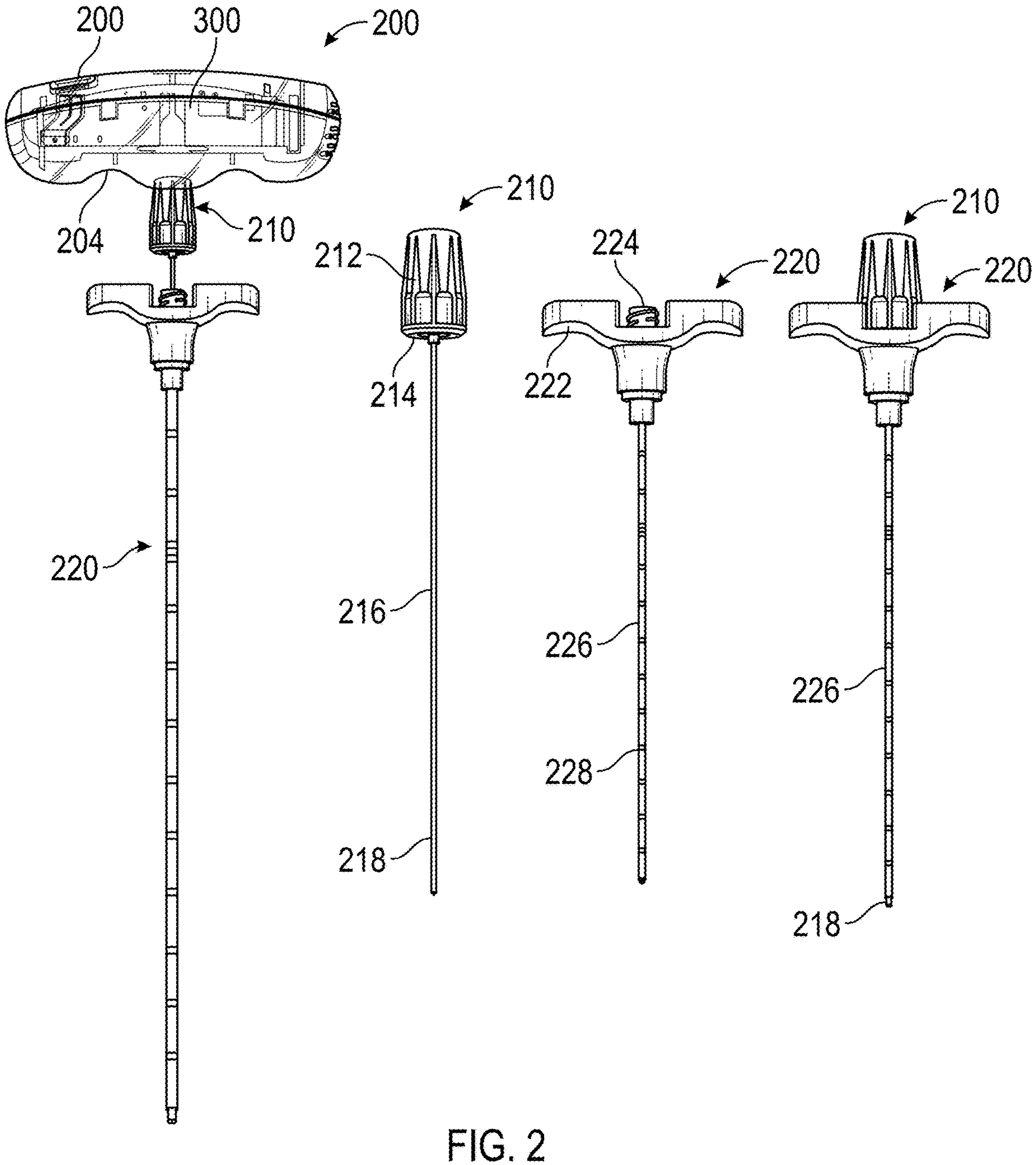
FIG. 2 illustrates an exemplary surgical tool for accessing the SI joint constructed in accordance with the principles of the present disclosure.

Referring now to FIG. 2, cannulated instrument 200 is provided. As shown in FIG. 2, cannulated instrument 200 may include housing 202 configured to be removably coupled to stylet 210, which may be inserted within and removably coupled to cannula 220, such that distal tip 218 of stylet 210 extends beyond the distal end of cannula 220. Housing 202 may include an interior cavity sized and shaped to house the electrical components (including controller 300, as described in further detail below with regard to FIG. 3) therein, and attachment portion 204 configured to removably receive hub 212 of stylet 210 and connection portion 222 of cannula 220, e.g., when stylet 210 is removably coupled to cannula 220. As shown in FIG. 2, housing 202 may form a T-shape when removably coupled to stylet 210 and cannula 220, and may be configured to receive a force applied thereon, e.g., via a surgical hammer tool, and transmit the force to stylet 210 and cannula 220 to permit penetration of the SI joint by distal tip 218 of stylet 210, and accordingly, the distal region of cannula 220. In some embodiments, housing 202 may define an ergonomic handle configured to permit a surgeon to manually apply force to cannulated instrument 200 to drill the pilot hole in the SI joint.

As shown in FIG. 2, stylet 210 may include hub 212, elongated shaft 216 extending from hub 216 and terminating at distal tip 218. Hub 212 may include mating portion 214 configured to be removably coupled to mating portion 224 of cannula 220. For example, mating portion 214 may include a threaded surface configured to removably engage with a corresponding threaded surface of mating portion 224 of cannula 220. Moreover, hub 212 may include an electrical interface to electrically coupled stylet 210 to the electrical components housed within housing 202 when stylet 210 is removably coupled to housing 202, to thereby transmit electrical signals between the electrical components housed within housing 202 and one or more pairs of electrodes disposed at/adjacent to distal tip 218, e.g., for transmitting signals generated by the electrical components to the electrodes and back to the electrical components.

Distal tip 218 of stylet 210 is configured to penetrate an anatomic portion such as the region that includes the SI joint and surrounding tissue, e.g., the ilium and sacrum, and includes one or more pairs of electrodes configured to sense electrical characteristics at distal tip 218, e.g., during penetration, as described in U.S. Pat. No. 7,580,743, the entire contents of which are incorporated by reference herein, which device is commercially available from the assignee of the present application under the tradename PediGuard®. For example, the pair of electrodes may be disposed on the distal surface at distal tip 218, and may include a first inner electrode (e.g., a negative pole) and a second outer electrode (e.g., a positive pole) spaced apart from the first inner electrode, e.g., via an insulation ring. The inner and outer electrodes may be cylindrical in shape and formed of conductive material. Alternatively, the outer electrode may be disposed coaxially around the inner electrode, with a layer of electrically insulating material interposed between the inner and outer electrodes. Accordingly, stylet 210 may provide data including, for example, tension (in Volts), tissue electrical resistivity (in Ohms), tissue electrical conductivity (in Siemens), simple moving average (SMA), weighted moving average (WMA), exponential moving average (EMA), polynomial regression data, and filtered signals with attenuation/amplification such as a transfer function (hysteresis) and/or an analog to binary/trinary transformation.

For example, as described in U.S. Patent Appl. Publ. No. 2022/0361896, the entire contents of which is incorporated herein by reference, an article entitled "Characterization of the electrical conductivity of bone and its correlation to osseous structure," by Balmer et al. in Scientific Reports (2018) 8:8601, describes conductivity values varying between approximately 9 mS/m for cortical bone and 230 mS/m for blood. A ratio of about 25 between the low value (cortical bone) and the high value (soft tissue, blood) is thus observed. In internal work carried out by the applicant using the PediGuard® device, the ratio between the highest and lowest resistance that the device was able to measure is 30, between 300 Ohms to 10 kOhms, which corresponds to electrical conductivities of about 50 milli-Siemens per meter to 1500 milli-Siemens per meter.

As shown in FIG. 2, cannula 220 may include connection portion 222 configured to be removably received by attachment portion 204 of housing 202, and mating portion 224 configured to be removably coupled to mating portion 214 of stylet 210, as described above. Moreover, cannula 220 may include cannulated shaft 226, and a lumen extending therethrough between mating portion 224 and an open distal end of cannula 220, the lumen sized and shaped to receive elongated shaft 216 of stylet 210 therethrough. Cannulated shaft 226 may have a length such that distal tip 218 of stylet 210 extends beyond the open distal end of cannula 220 when stylet 210 is removably coupled to cannula 220. As shown in FIG. 2, the outer surface of cannulated shaft 226 further may include markings 228 disposed axially along the length of cannulated shaft 228, to thereby indicate the depth of penetration of the SI joint by cannulated instrument 200.

Figure 3:
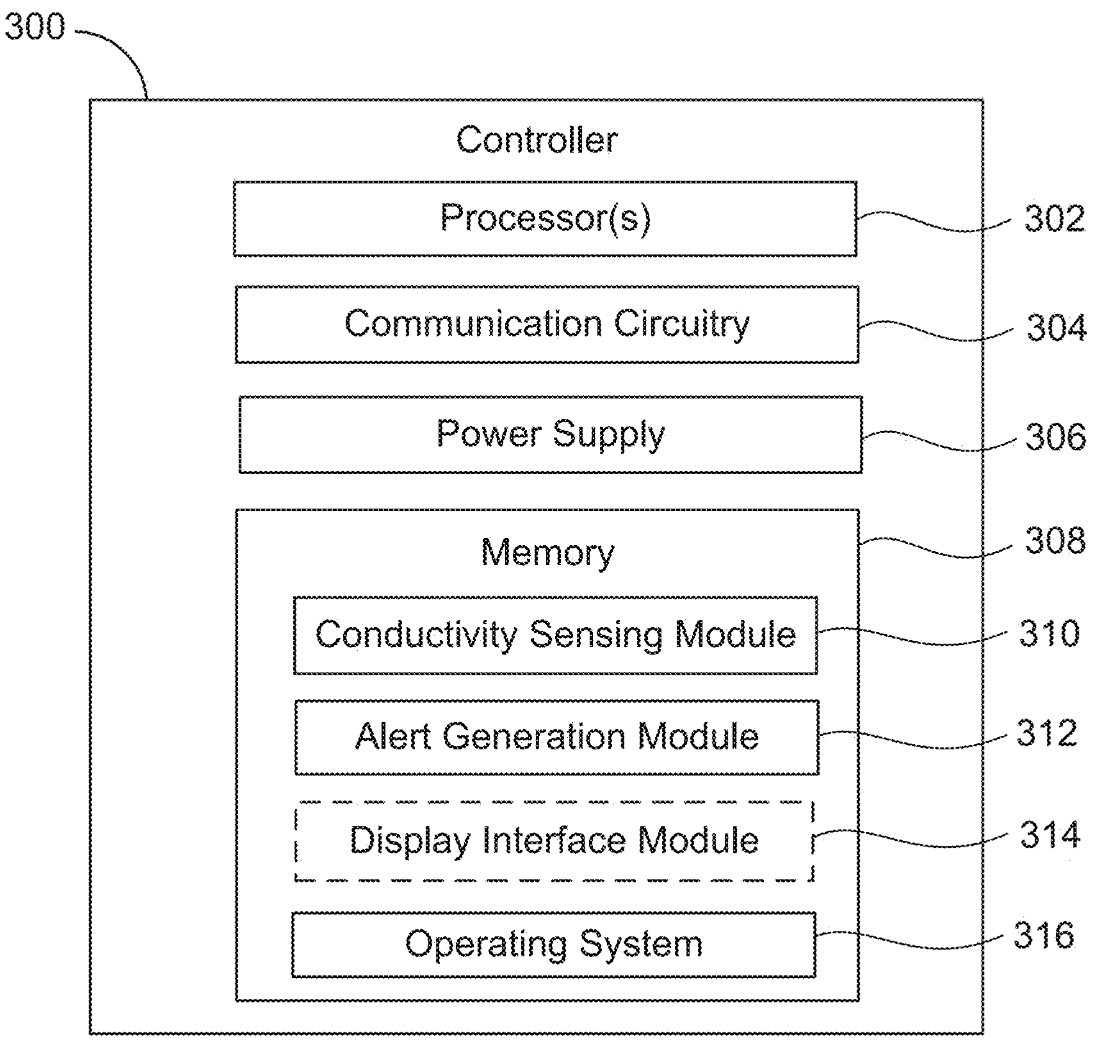
FIG. 3 is a schematic diagram of an exemplary controller constructed in accordance with the principles of the present disclosure.
Figure 4:
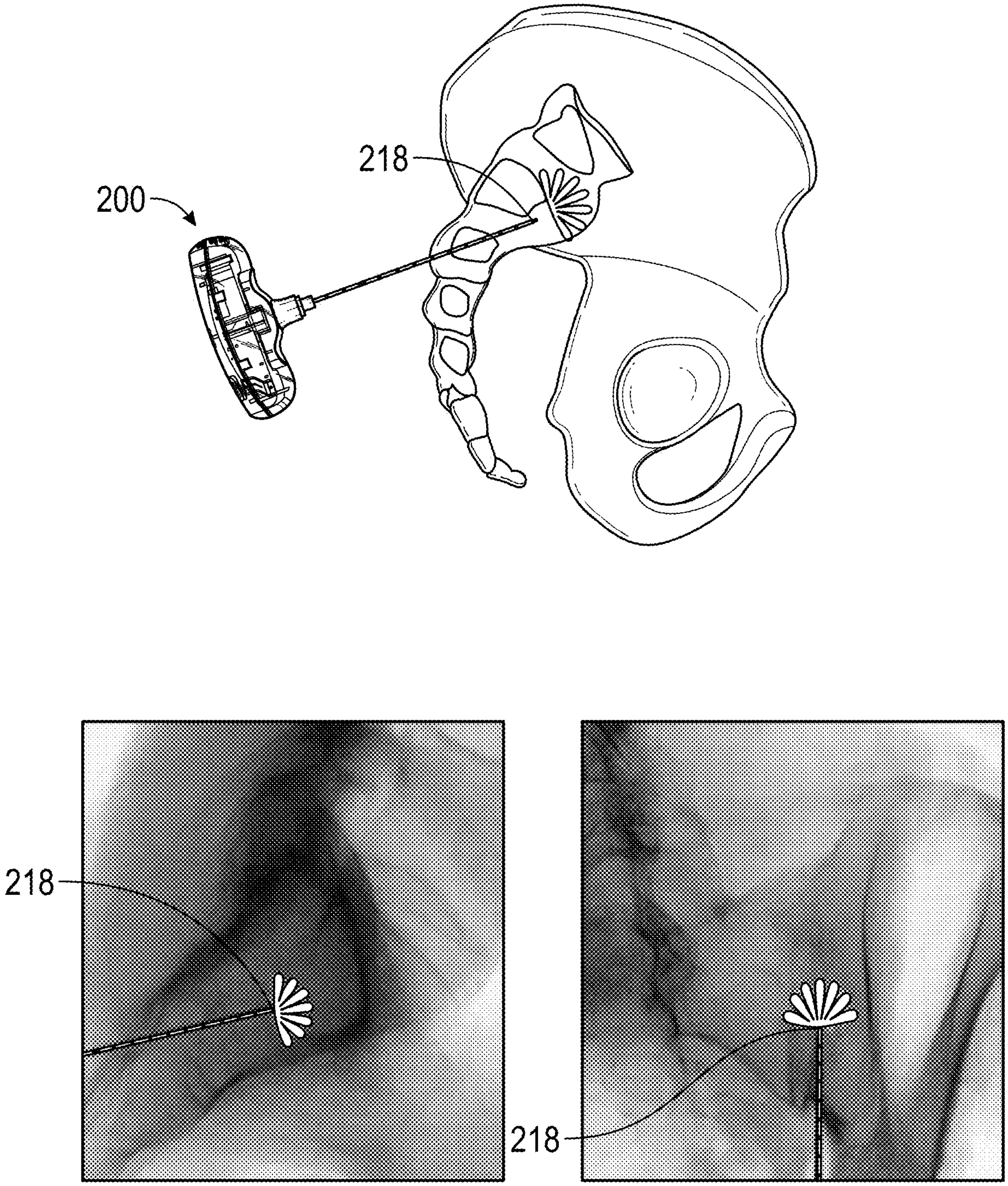
FIG. 4 illustrates insertion of the distal tip of the surgical tool into the SI joint via a posterior approach.

Referring now to FIG. 3, components that may be included in controller 300 used in conjunction with cannulated instrument 200, and optionally with display device 150, is provided. Controller 300 may be operatively coupled to the electrical components of cannulated instrument 200 and display device 150, such that controller 300 may receive signals indicative of electrical conductivity measurements from cannulated instrument 200, e.g., based on electrical conductivity of the surrounding tissue (including bone) during penetration, and generate an alert based on the signals. For example, as shown in FIG. 4, cannulated instrument 200 may sense electrical conductivity of the surrounding tissue as cannulated instrument 200 is advanced into the SI joint. As shown in FIG. 3, controller 300 may include one or more processors 302, communication circuitry 304, power supply 306, and/or memory 308. Memory 308 may be RAM, ROM, Flash, or other known memory, or some combination thereof, and preferably includes storage in which data may be selectively saved. One or more electrical components and/or circuits may perform some of or all the roles of the various components described herein. Although described separately, it is to be appreciated that electrical components need not be separate structural elements. For example, controller 300 and communication circuitry 304 may be embodied in a single chip. In addition, while controller 300 is described as having memory, a memory chip(s) may be separately provided.

Processor 302 may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. The controller also may be implemented as a combination of computing devices, e.g., a combination of a DSP and a microprocessor, a plurality of microprocessors, one or more microprocessors in conjunction with a DSP core, or any other such configuration. Controller 300, in conjunction with firmware/software stored in the memory may execute an operating system (e.g., operating system 318), such as, for example, Windows, Mac OS, Unix or Solaris 5.10. Controller 300 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuitry 304 may include circuitry that allows controller 300 to communicate with the electronic components of cannulated instrument 200 (e.g., the conductivity meter and alert device) including the electrodes of stylet 210, and optionally, with the electronic components of display device 150. Communication circuitry 304 may be configured for wired and/or wireless communication over a network such as the Internet, a telephone network, a Bluetooth network, and/or a WiFi network using techniques known in the art. Communication circuitry 304 may be a communication chip known in the art such as a Bluetooth chip and/or a WiFi chip. Communication circuitry 304 permits controller 300 to transfer information, such as signals indicative of electrical conductivity measurements from cannulated instrument 200, locally and/or to a remote location such as a server.

Power supply 306 may be designed to supply power to the electrical components of cannulated instrument 200. Memory 308, which is one example of a non-transitory computer-readable medium, may be used to store operating system (OS) 316, conductivity sensing module 310, alert generation module 312, and optional display interface module 312. The modules are provided in the form of computer-executable instructions that may be executed by processor 302 for performing various operations in accordance with the disclosure.

Figure 5:
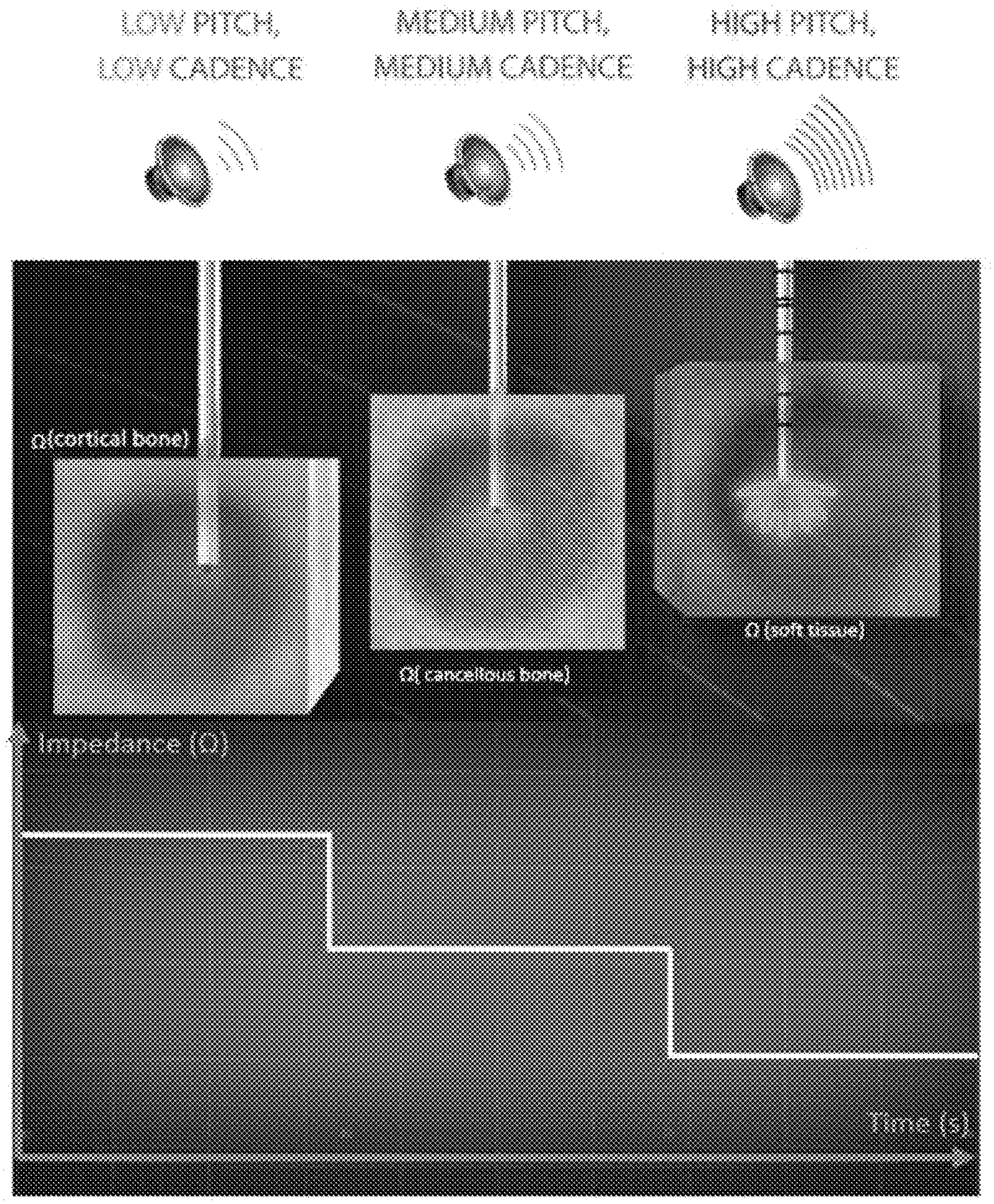
FIG. 5 illustrates electrical conductivity and corresponding exemplary alerts along an insertion trajectory across various tissue types in accordance with the principles of the present disclosure.

Conductivity sensing module 310 may be executed by processor 302 for receiving one or more signals from the electrodes of cannulated instrument 200 indicative of measured electrical conductivity as the distal tip 218 penetrates the anatomic portion, e.g., the SI joint. Specifically, conductivity sensing module 310 may determine a measurement parameter related to the electrical characteristic, e.g., voltage, an intensity of the electric current, conductivity or resistivity, based on a measurement electric current(s) induced by the applied voltage(s). Accordingly, conductivity sensing module 310 may measure the electrical conductivity of the tissue (including bone, e.g., the ilium or sacrum), and/or the electrical conductivity (based on the electrical conductivity) surrounding distal tip 218 as it penetrates the anatomic portion in real-time, which may be used to distinguish the different tissues distal tip 218 passes through during the drilling process. For example, as shown in FIG. 5, which illustrates exemplary electrical impedance measurements acquired during a drilling process over time, the impedance signal is high (low electrical conductivity) in the cortical layers compared to the impedance signal detected in the cancellous layers, and decreases significantly (high electrical conductivity) once cannulated instrument 200 intersects soft tissue (e.g., fluid within the intra-articular space of the SI joint). Accordingly, these tissue discrimination characteristics are suitable for the detection of perforations (e.g., cortex perforations).

Alert generation module 312 may be executed by processor 302 for generating an alert signal indicative of the level of electrical conductivity measured by cannulated instrument 200 in real-time during penetration of the anatomic portion by the cannulated instrument, which is indicative of the tissue type (including bone) that distal tip 218 is in contact with in real-time. Alert generation module 312 further may cause the alert device of cannulated instrument 200 (or optionally display device 150) to emit an alert, e.g., an audible, visual, and/or tactile alert, based on the alert signal. For example, alert generation module 312 may cause the alarm device, e.g., an audio speaker, to continuously emit an audible alert signal pitch-modulated and/or cadence-modulated, which may vary based on the change in electrical conductivity measured by conductivity. Additionally, or alternatively, alert generation module 312 may cause the alarm device, e.g., LED light, to continuously emit a visual signal (illumination) frequency-modulated (e.g., rate of blinking), intensity-modulated (e.g., brightness) and/or color-modulated, which may similarly vary based on the change in electrical conductivity measured by conductivity sensing module 310. Accordingly, one or more parameters of the alert (e.g., pitch, cadence, frequency, intensity/brightness, color, etc.) may change incrementally proportionally based on changes of the sensed electrical conductivity, such that the surgeon may interpret the alert and stop advancement of the cannulated instrument into the patient when the emitted alert indicates that the distal tip of the cannulated instrument is undesirably in contact with tissue (including bone) surrounding the SI joint.

As shown in FIG. 5, the audio signal may have a low pitch (and/or cadence) in the cortical layers compared to the audio signal generated in the cancellous layers, and increases significantly once cannulated instrument 200 intersects soft tissue (e.g., fluid within the intra-articular space of the SI joint). Alternatively, as will be understood by a person having ordinary skill in the art, the audio signal may have a low pitch (and/or cadence) in soft tissue compared to the audio signal generated in the cancellous layers, and may increase significantly once cannulated instrument 200 intersects the cortical layers.

Display interface module 316 may be executed by processor 302 for rendering and transmitting data to display device 150 operatively coupled to controller 300, for displaying information associated with the transmitted data. For example, display interface module 316 may cause information indicative of the electrical conductivity measured by conductivity sensing module 310 to be displayed. In addition, display interface module 316 may cause display device 150 to emit an audible and/or visual (e.g., graphical) alert (based on the alert signal generated by alert generation module 312) that varies based on the change in electrical conductivity measured by conductivity sensing module 310.

Figure 6A:
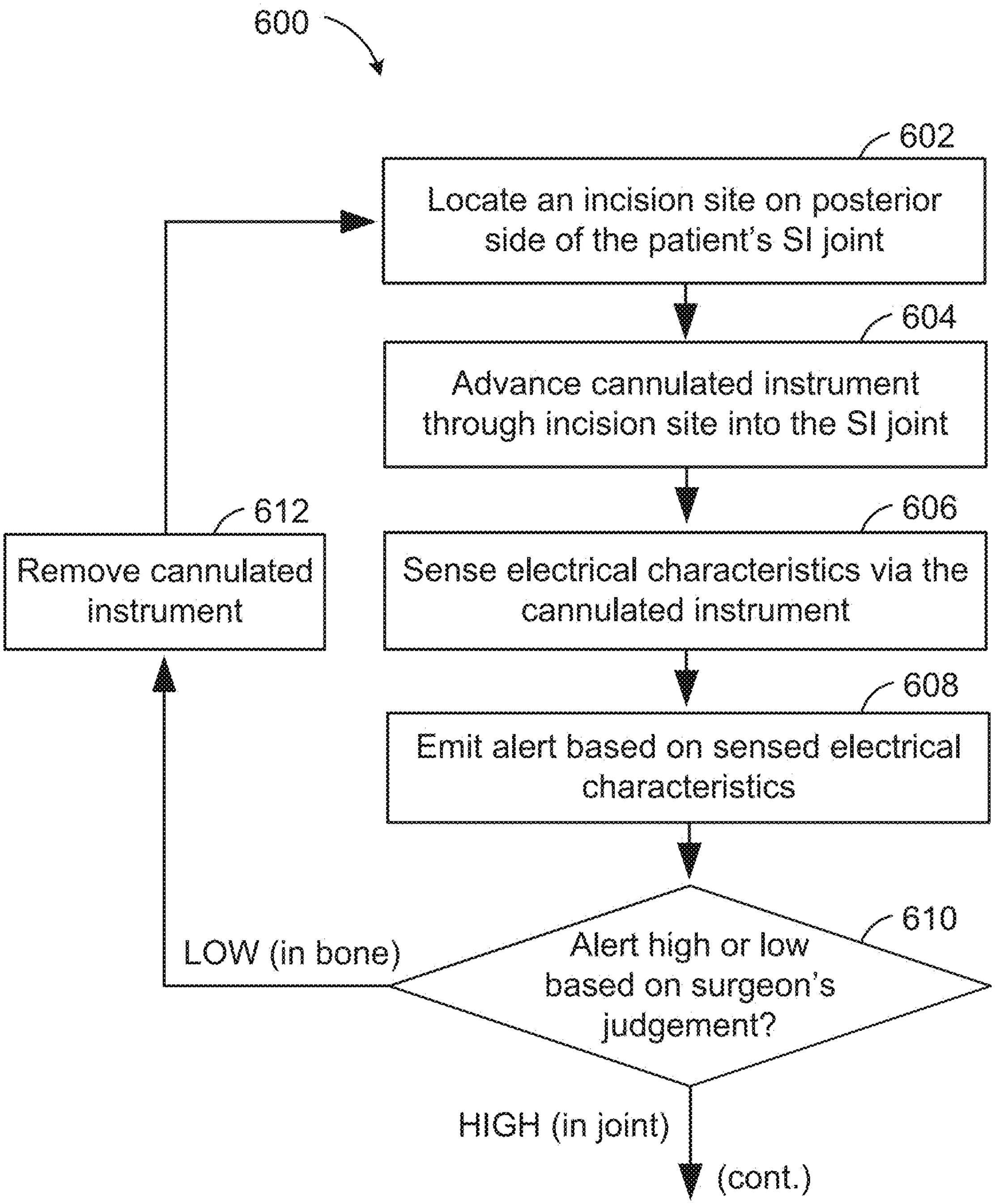
FIG. 6A is a flow chart illustrating an exemplary method for locating an incision site to access the SI joint using the system of FIG. 1.
Figure 6B:
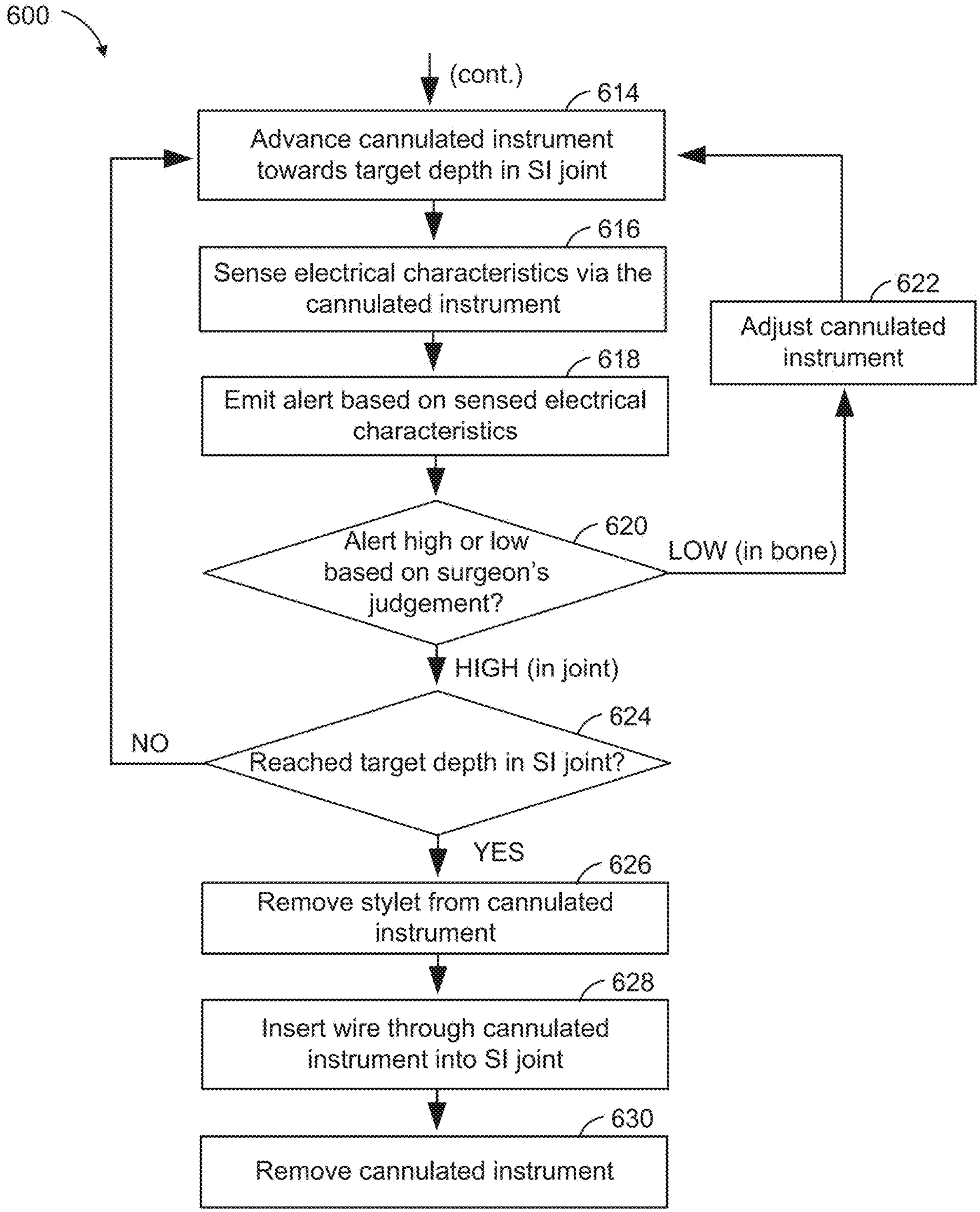
FIG. 6B is a flow chart illustrating an exemplary method for accessing a target location within the SI joint using the system of FIG. 1.
Figure 7A:
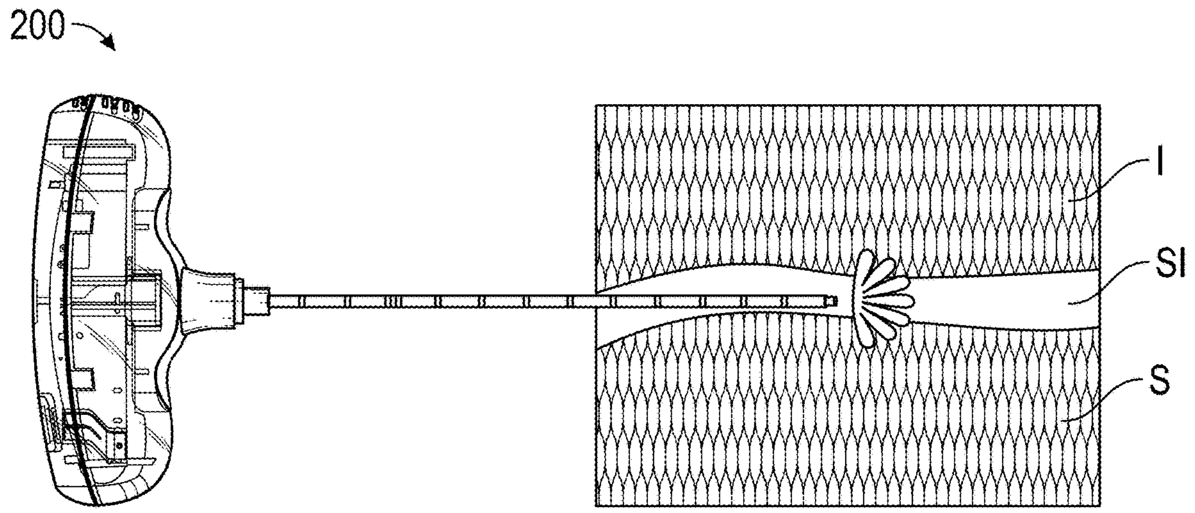
FIGS. 7A to 7E illustrate exemplary method steps for accessing the SI joint using the system of FIG. 1.

Referring now to FIGS. 6A and 6B, exemplary method 600 for accessing the SI joint via a posterior-oblique approach using system 100 is provided. Method 600 may include steps for locating the desired entry point into the SI, as shown in FIG. 6A, and steps for reaching the target depth in the SI joint, as shown in FIG. 6B. The patient may initially be prepared for surgery, e.g., positioning the patient in a prone position to provide the surgeon access to the SI joint, administering general or local anesthesia, etc. As shown in FIG. 6A, at step 602, the surgeon may locate an incision site on the posterior side of the patient's SI joint for access to the SI joint based on the location of one or more anatomical landmarks. As described above, the surgeon may use, e.g., the right posterior iliac crest, as an anatomical landmark to locate the patient's SI joint, e.g., by blunt finger palpitation and/or via imaging (e.g., x-ray), or any other suitable method. At step 604, distal tip 218 of cannulated instrument 200 may be used to create an incision at the incision site and advanced through the incision into the SI joint, e.g., manually or via a surgical hammer tool, under fluoroscopic visualization, and simultaneously, at step 606, the electrodes disposed at distal tip 218 may continuously sense electrical characteristics, e.g., electrical conductivity, of tissue in contact with distal tip 218, as cannulated instrument 200 is advanced into the SI joint, as shown in FIG. 7A. Moreover, cannulated instrument 200 may generate an alert signal indicative of the sensed electrical characteristics.

Figure 7B:
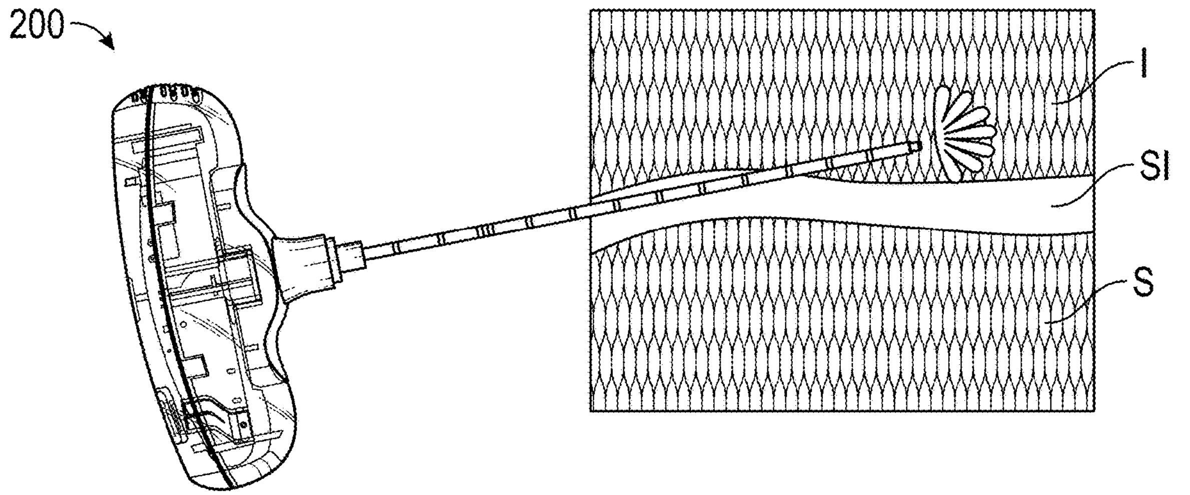

Referring again to FIG. 6A, at step 608, which may occur simultaneously with steps 604 and 606, the system may emit an audible and/or visual alert (e.g., via the alert device housing within housing 202 of cannulated instrument 200 and/or display device 150) indicative of the electrical conductivity sensed by cannulated instrument 200, and accordingly, the type of tissue in contact with distal tip 218 in real-time, e.g., based on the alert signal. As described above, the alert may be emitted continuously during the drilling procedure, such that the surgeon may deduce, e.g., via human signal interpretation, when the distal tip of the cannulated instrument undesirably contacts surrounding tissue (e.g., the ilium or sacrum, as shown in FIG. 7B), based on a change in the alert parameter(s) (e.g., pitch, cadence, frequency, color, etc.).

Accordingly, at step 610, based on the surgeon's interpretation of the alert, the surgeon may determine whether the alert indicates a significantly low electrical conductivity (e.g., low pitch/cadence of an audible alert and/or a low blinking frequency/brightness of a visual alert), or a significantly high electrical conductivity (e.g., high pitch/cadence of an audible alert and/or a high blinking frequency/brightness of a visual alert). If the surgeon interprets that the alert indicates a significantly low electrical conductivity, the surgeon may deduce that the distal tip of the cannulated instrument is in contact with an undesirable tissue (e.g., the ilium or sacrum), and at step 612, the surgeon may stop penetration via the cannulated instrument and remove the cannulated instrument from the patient's body. The surgeon may return to step 602 and re-locate an incision site on the posterior side of the patient's SI joint for access to the SI joint, e.g., based on the location of one or more anatomical landmarks. Additionally, or alternatively, at step 602, the surgeon may adjust the angle/orientation of the cannulated instrument relative to the incision site prior to further advancement of the cannulated instrument at step 604.

If the surgeon interprets that the alert indicates a significantly high electrical conductivity, the surgeon may deduce that the distal tip of the cannulated instrument is in contact with soft tissue, e.g., fluid within the intra-articular space of the SI joint, and as shown in FIG. 6B, at step 614, the surgeon may proceed to advancing the cannulated instrument within the SI joint to reach the target depth in the SI joint. At step 616, the electrodes disposed at distal tip 218 may simultaneously continuously sense electrical characteristics, e.g., electrical conductivity, of tissue in contact with distal tip 218 as cannulated instrument 200 is advanced into the SI joint, as shown in FIG. 7A. As described above, cannulated instrument 200 may generate an alert signal indicative of the sensed electrical characteristics.

At step 618, which may occur simultaneously with steps 614 and 616, the system may continuously emit an audible and/or visual alert indicative of the electrical conductivity sensed by cannulated instrument 200, and accordingly, the type of tissue in contact with distal tip 218 in real-time, e.g., based on the alert signal. At step 620, based on the surgeon's interpretation of the alert, the surgeon may determine whether the alert indicates a significantly low electrical conductivity or a significantly high electrical conductivity, as described above. If the surgeon interprets that the alert indicates a significantly low electrical conductivity, the surgeon may deduce that the distal tip of the cannulated instrument is in contact with an undesirable tissue (e.g., the ilium or sacrum), and at step 622, the surgeon may stop penetration via the cannulated instrument and readjust the position/orientation/angle of the cannulated instrument relative to the SI joint, e.g., under fluoroscopy, to redirect the cannulated instrument prior to proceeding with the drilling procedure at step 614 so as to avoid contacting/disrupting the surrounding tissue.

Figure 7C:
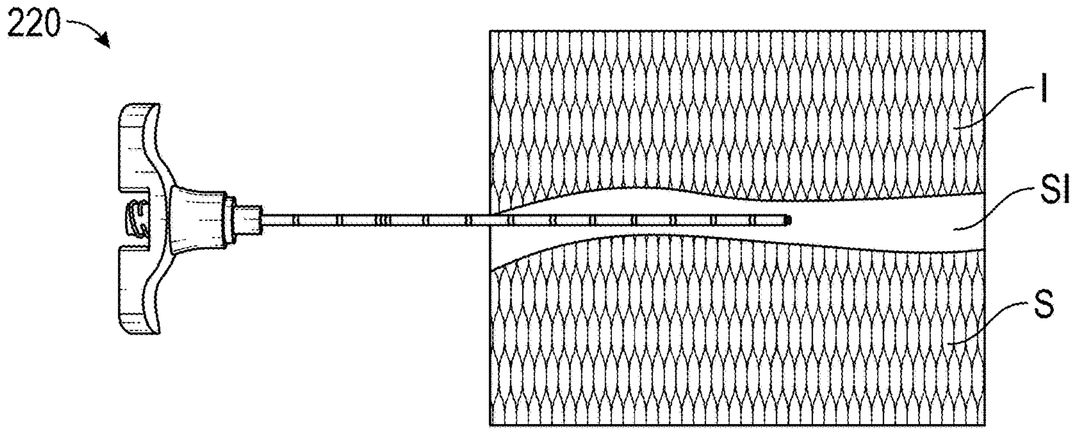
Figure 7D:
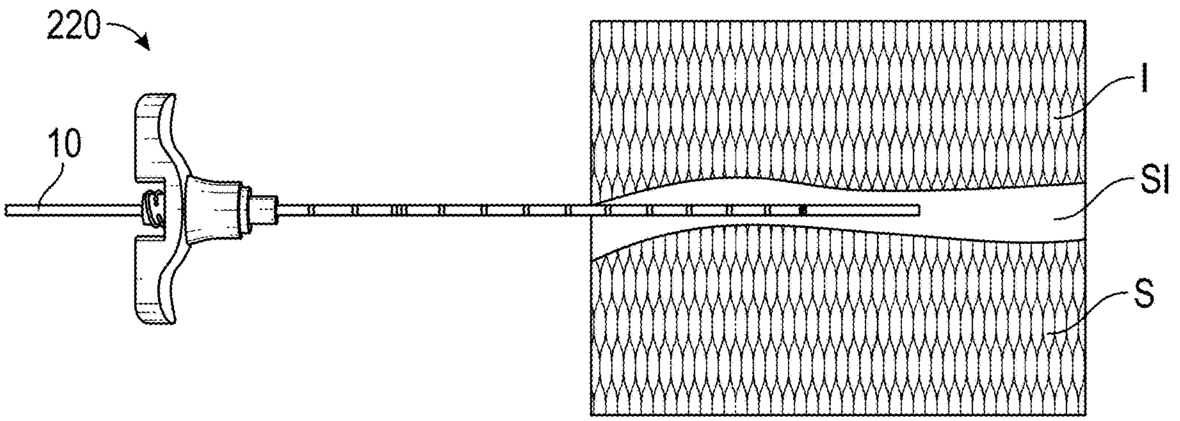
Figure 7E:
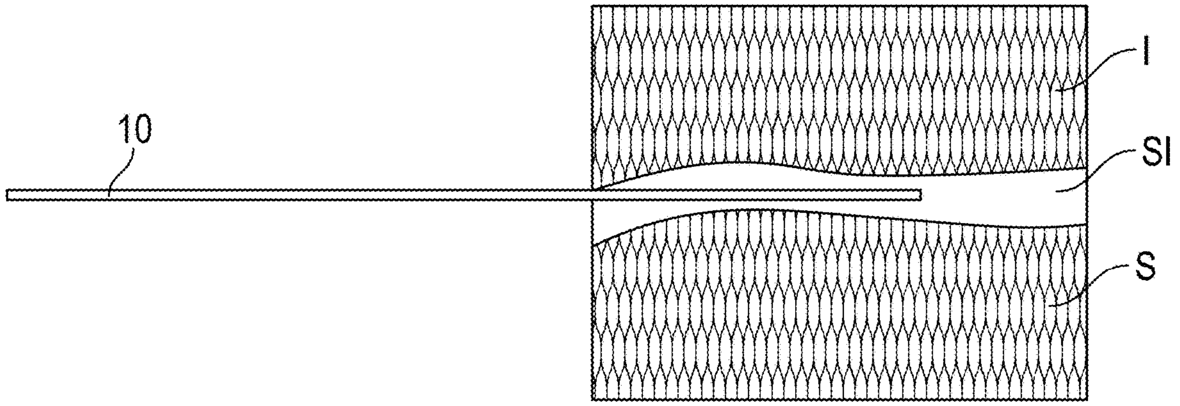

If the surgeon interprets that the alert indicates a significantly high electrical conductivity, the surgeon may deduce that the distal tip of the cannulated instrument is still in contact with soft tissue of the SI joint, and at step 624, the surgeon may determine whether distal tip 18 is in the target location within the SI joint (e.g., at a target depth within the SI joint, indicated by markings 228 of cannula 220 of cannulated instrument 200). If the surgeon determines that distal tip 18 is not in the target location within the SI joint, the surgeon may continue to advance the cannulated instrument into the SI joint at step 614. If the surgeon determines that distal tip 18 is in the target location within the SI joint, at step 626, housing 202 may be decoupled and removed from cannula 220 and stylet 210, and stylet 210 may be decoupled and removed from cannula 220, leaving cannula 220 at the target location within the SI joint, as shown in FIG. 7C. At step 628, K-wire 10 may be inserted through the lumen of cannula 220, such that the distal end of K-wire 10 is disposed at the target location within the SI joint, as shown in FIG. 7D. At step 630, cannula 220 may be removed from the patient, leaving K-wire 10 at the target location within the SI joint, such that the proximal end of K-wire 10 extends external to the patient, as shown in FIG. 7E. Accordingly, as described above, one or more additional surgical tools/implants may then be advanced over K-wire 10 to access the target location into or across the SI joint for performing a subsequent procedure.

Figure 8A:
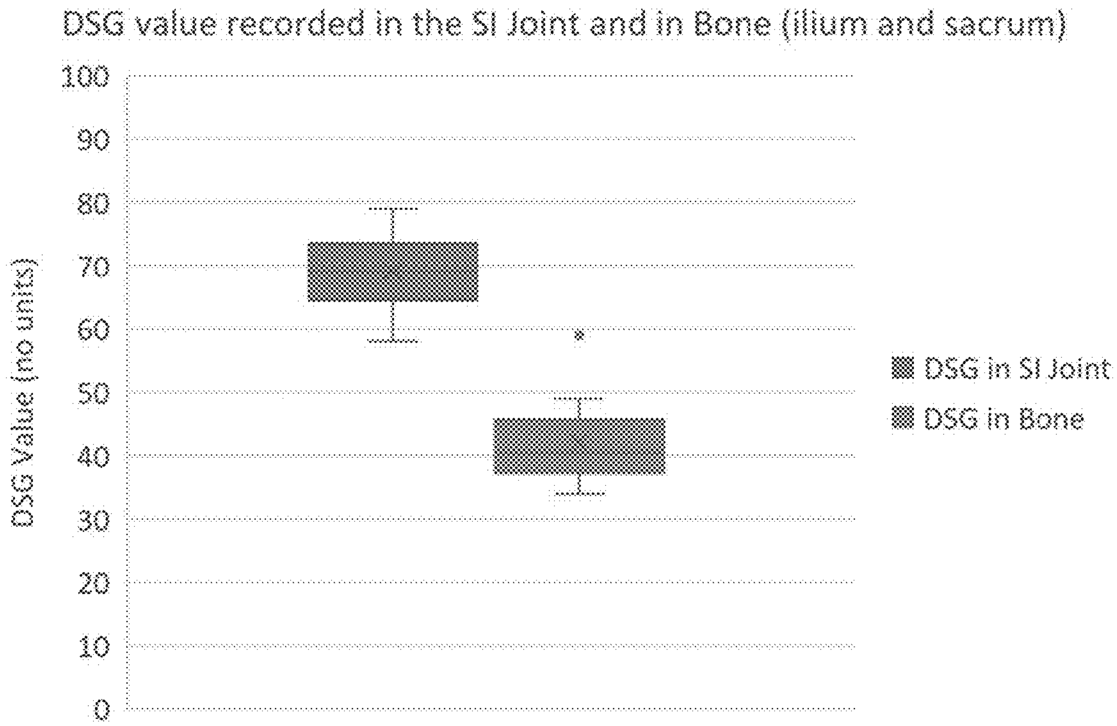
FIGS. 8A and 8B are graphs illustrating electrical characteristics sensed by the surgical tool in various tissue types.
Figure 8B:
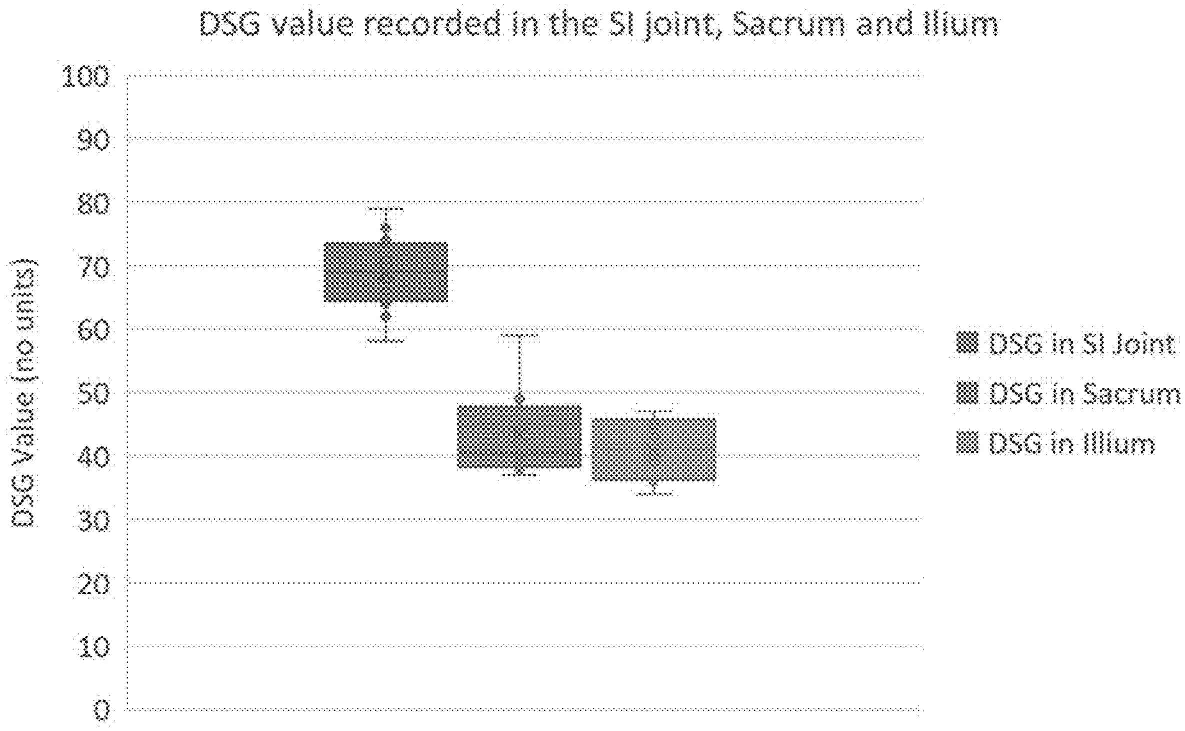

Referring now to FIGS. 8A and 8B, the differences in electrical conductivity for various tissue types as measured by a prototype of the cannulated instrument described herein, is illustrated. As shown in FIGS. 8A and 8B, a proprietary unit of measure under the commercial name Dynamic Surgical Guidance (DSG) is used to represent a unitless signal that is representative of the electrical conductivity in Siemens/m. As shown in FIG. 8A, the DSG signal detected by the cannulated instrument when in contact with soft tissue in the SI joint (e.g., fluid within the intra-articular space of the SI joint) is significantly higher than the DSG signal detected by the cannulated instrument when in contact with bone (e.g., the ilium or the sacrum). Similarly, as shown in FIG. 8B, the DSG signal detected by the cannulated instrument when in contact with soft tissue in the SI joint (e.g., fluid within the intra-articular space of the SI joint) is significantly higher than both of the DSG signals detected by the cannulated instrument when in contact with the sacrum or the ilium, with the electrical conductivity signal slightly higher when in contact with the sacrum than the ilium.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for accessing a patient's Sacroiliac (SI) joint via a posterior approach, the method comprising:

identifying an anatomical landmark associated with the patient's SI joint to locate the SI joint, the anatomical landmark disposed on a posterior side of the SI joint;

identifying an incision site on the posterior side of the SI joint based on the anatomical landmark;

advancing a distal tip of a cannulated instrument through the incision site towards a target position in an intra-articular space of the SI joint while monitoring an alert signal generated by the cannulated instrument, the alert signal indicative of electrical conductivity of tissue in contact with the distal tip in real-time;

removing, if the alert signal indicates low electrical conductivity, the cannulated instrument from the patient's SI joint and reinserting the distal tip of the cannulated instrument through another identified incision site towards the target position while monitoring the alert signal generated by the cannulated instrument;

advancing, if the alert signal indicates high electrical conductivity, the distal tip of the cannulated instrument towards the target location;

adjusting, if the alert signal indicates low electrical conductivity, a position of the cannulated instrument relative to the SI joint to redirect the cannulated instrument towards the target location; and advancing, if the alert signal indicates high electrical conductivity, the distal tip of the cannulated instrument until the distal tip of the cannulated instrument is disposed at the target location.

2. The method of claim 1, wherein identifying the anatomical landmark associated with the patient's SI joint comprises identifying a right posterior iliac crest of the patient.

3. The method of claim 1, wherein advancing the distal tip of the cannulated instrument through the incision site to the target position in the intra-articular space of the SI joint comprises manually applying a force to a proximal end of the cannulated instrument.

4. The method of claim 1, wherein advancing the distal tip of the cannulated instrument through the incision site to the target position in the intra-articular space of the SI joint comprises applying a force to a proximal end of the cannulated instrument via a surgical hammer tool.

5. The method of claim 1, wherein monitoring the alert signal generated by the cannulated instrument comprises monitoring at least one of an audible or visual alert emitted based on the alert signal.

6. The method of claim 5, wherein at least one of a pitch or cadence of the audible alert is based on the electrical conductivity of tissue in contact with the distal tip in real-time.

7. The method of claim 5, wherein at least one of a frequency, intensity, or color of the visual alert is based on the electrical conductivity of tissue in contact with the distal tip in real-time.

8. The method of claim 1, wherein the alert signal is indicative of a type of tissue in contact with the distal tip of the cannulated instrument in real-time.

9. The method of claim 8, wherein the alert signal indicates that the distal tip of the cannulated instrument is in contact with at least one of an ilium or a sacrum when the alert signal indicates low electrical conductivity.

10. The method of claim 8, wherein the alert signal indicates that the distal tip of the cannulated instrument is in contact with soft tissue of the SI joint when the alert signal indicates high electrical conductivity.

11. The method of claim 1, wherein the cannulated instrument is configured to transmit data indicative of the electrical conductivity to an external display device.

12. The method of claim 11, wherein the external display device is configured to graphically display the data indicative of the electrical conductivity.

13. The method of claim 11, wherein monitoring the alert signal generated by the cannulated instrument comprises monitoring at least one of an audible or visual alert emitted by the external display device based on the alert signal.

14. The method of claim 1, wherein adjusting the position of the cannulated instrument relative to the SI joint to redirect the cannulated instrument towards the target location comprises:

removing the cannulated instrument from the patient;

reorienting the distal tip of the cannulated instrument relative to the SI joint; and reinserting the distal tip of the cannulated instrument through the incision site towards the target position in the intra-articular space of the SI joint.

15. The method of claim 1, wherein adjusting the position of the cannulated instrument relative to the SI joint to redirect the cannulated instrument towards the target location comprises reorienting the distal tip of the cannulated instrument relative to the SI joint.

16. The method of claim 1, wherein the distal tip of the cannulated instrument comprises one or more pairs of electrodes configured to sense the electrical conductivity of tissue in contact with the distal tip.

17. The method of claim 1, further comprising visualizing advancement of the cannulated instrument through the SI joint via fluoroscopy.

18. The method of claim 1, further comprising monitoring a depth of advancement of the cannulated instrument through the SI joint via a plurality of markers disposed on an outer surface of the cannulated instrument.

19. The method of claim 1, further comprising:

inserting a distal end of a K-wire through a lumen of the cannulated instrument to the target position in the intra-articular space of the SI joint, such that a proximal end of the K-wire extends external to the patient; and removing the cannulated instrument from the patient.

20. The method of claim 19, wherein the cannulated instrument comprises a cannula and a stylet removably disposed within a lumen of the cannula, the stylet comprising the distal tip of the cannulated instrument, the method further comprising:

removing the stylet from the lumen of the cannula when the distal tip is disposed at the target position in the intra-articular space of the SI joint, wherein inserting the distal end of the K-wire through the lumen of the cannulated instrument to the target position in the intra-articular space of the SI joint comprises inserting the distal end of the K-wire through the lumen of the cannula.

21. The method of claim 19, further comprising advancing a surgical tool over the K-wire to the target position in the intra-articular space of the SI joint to perform a surgical procedure at the target position.

22. The method of claim 19, further comprising advancing a spinal implant over the K-wire to the target position into or across the intra-articular space of the SI joint.

* * * * *